（12） United States Patent
Galland et al.

(10) Patent No.: US 9,533,015 B2
(45) Date of Patent: Jan. 3, 2017

(54) LACTOCOCCUS LACTIS STRAINS

(71) Applicants:Centro De Investigación En Alimentacion Y Desarrollo, A.C. (CIAD); Belinda Vallejo Galland, Hermosillo, Sonara (MX); Aarón Fernando González Córdova, Hermosillo, Sonora (MX)

(72) Inventors: Belinda Vallejo Galland, Sonora (MX); Aarón Fernando González Córdova, Sonara (MX); Jóse Carlos Rodríguez Figueroa, Sonora (MX)

(73) Assignees: Centro De Investigación En Alimentación Y Desarrollo, A.C. (CIAD), Hermosillo (MX); Belinda Vallejo Galland, Hermosillo (MX); Aarón Fernando González Córdova, Hermosillo (MX)

( * ) Notice: Subject to any disclaimer, the term of this patent is extended or adjusted under 35 U.S.C. 154(b) by 0 days.

(21) Appl. No.: 14/525,090

(22) Filed: Oct. 27, 2014

(65) Prior Publication Data

US 2015/0051159 A1   Feb. 19, 2015

Related U.S. Application Data

(62) Division of application No. 14/509,925, filed on Oct. 8, 2014, now Pat. No. 9,295,701, which is a division
(Continued)

(51) Int. Cl.
  *C12N 1/20*  (2006.01)
  *A61K 35/744*  (2015.01)
(Continued)

(52) U.S. Cl.
  CPC ............. *A61K 35/744* (2013.01); *A23C 9/123* (2013.01); *A23C 9/1234* (2013.01); *A23C 9/152* (2013.01);
(Continued)

(58) Field of Classification Search
  CPC .................................. C12N 1/20; A23C 9/123
  See application file for complete search history.

(56) References Cited

U.S. PATENT DOCUMENTS

2005/0031602 A1   2/2005   Flambard
2007/0203060 A1   8/2007   Sidelman

FOREIGN PATENT DOCUMENTS

WO   WO 2007096855   8/2007

OTHER PUBLICATIONS

Rodríguez-Figueroa, J. C., González-Córdova, A. F., Astiazaran-García, H., Hernández-Mendoza, A. and Vallejo-Cordoba, B. 2013. Antihypertensive and hypolipidemic effect of milk fermented by specific Lactococcus lactis strains. ISSN: 0022-0302. Journal of Dairy Science. 96(7): 4094-4099.
(Continued)

*Primary Examiner* — Rosanne Kosson
(74) *Attorney, Agent, or Firm* — Perkins Coie LLP; Viola T. Kung

(57) ABSTRACT

New *Lactococcus lactis* strains, NRRL B-50571 and NRRL B-50572, and a bacterial preparation containing the same, have the ability to produce bioactive peptides that reduce blood pressure, lower LDL-cholesterol (bad cholesterol) and present antioxidant properties for better cardiovascular health. These biologically active peptides may be produced within the food for the production of a food product, such as a functional food, or they may be produced from protein
(Continued)

sources and subsequently added to a food as part of the formulation or as part of a food supplement or a pharmaceutical preparation.

5 Claims, 12 Drawing Sheets

Related U.S. Application Data of application No. 13/629,398, filed on Sep. 27, 2012, now Pat. No. 8,865,155.

(60) Provisional application No. 61/540,979, filed on Sep. 29, 2011.

(51) Int. Cl.
| | |
|---|---|
| *C12P 21/00* | (2006.01) |
| *C12P 21/06* | (2006.01) |
| *C12R 1/00* | (2006.01) |
| *A23C 9/123* | (2006.01) |
| *A61K 35/74* | (2015.01) |
| *A23C 9/152* | (2006.01) |
| *A23L 2/52* | (2006.01) |
| *A61K 35/742* | (2015.01) |
| *A61K 38/08* | (2006.01) |
| *A61K 38/10* | (2006.01) |
| *A61K 35/00* | (2006.01) |

(52) U.S. Cl.
CPC .............. *A23L 2/52* (2013.01); *A23L 33/135* (2016.08); *A61K 35/74* (2013.01); *A61K 35/742* (2013.01); *A61K 38/08* (2013.01); *A61K 38/10* (2013.01); *C12N 1/20* (2013.01); *C12P 21/00* (2013.01); *C12P 21/06* (2013.01); *C12R 1/00* (2013.01); *A23V 2002/00* (2013.01); *A23Y 2240/41* (2013.01); *A61K 2035/115* (2013.01)

(56) References Cited

OTHER PUBLICATIONS

Rodríguez-Figueroa, J. C., González-Córdova, A. F., Astiazaran-García, H. and Vallejo-Cordoba, B. 2013. Hypotensive and heart rate lowering effects in rats receiving milk fermented by specific Lactococcus lactis strains. ISSN: 0007-1145.British J. Nutr., 109, 827-833.

Rodríguez-Figueroa, J. C., González-Córdova, A. F., Torres-Llanez, M. J., Garcia, H. S. and Vallejo-Cordoba, B. 2012. Novel angiotensin I-converting enzyme inhibitory peptide produced in fermented milk by specific wild Lactococcus lactis strains. ISSN 0022-0302. Journal of Dairy Science. 95(10): 5536-5543.

Fugslang, et al., "Cardiovascular Effects of Fermented Milk Containing Angiotensin-Converting Enzyme Inhibitors Evaluated in Permanently Catheterized, Spontaneously Hypertensive Rats", Applied and Environmental Microbiology 68(7), Jul. 2002, pp. 3566-3569.

Gutierrez-Mendez, et al., "Phenotypic and genotypic characteristics of Lactococcus lactis strains isolated from different ecosystems", Canadian Journal of Microbiology (56), May 2010, pp. 432-439.

Rodriguez-Figueroa, et al., "Angiotensin-converting enzyme inhibitory activity of milk fermented by wild and industrial Lactococcus lactis strains", Journal of Dairy Sicence; 93(11), Nov. 2010, pp. 5032-5038.

Torres-Llanez, et al., "Angiotensin-converting enzyme inhibitory activity in Mexican Fresco cheese", Journal of Dairy Science 94(8), Jul. 2011, pp. 3974-3800.

LACTOCOCCUS LACTIS STRAINS

CROSS REFERENCE TO RELATED APPLICATIONS

This application is a divisional application of U.S. application Ser. No. 14/509,925, filed Oct. 8, 2014; which is a divisional application of U.S. application Ser. No. 13/629,398, filed Sep. 27, 2012, now U.S. Pat. No. 8,865,155; which claims the benefit of U.S. Provisional Application No. 61/540,979, filed Sep. 29, 2011; the contents of the above applications are incorporated by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Oct. 27, 2014, and a size of 3.8 kilobytes. The Sequence Listing filed via EFS-Web is part of the specification and is hereby incorporated in its entirety by reference herein.

FIELD OF THE INVENTION

In general, the invention relates to *Lactococcus lactis* strains for the production of bioactive peptides. More particularly, the invention relates to *Lactococcus lactis* strains, and bacterial preparations thereof, for the production of bioactive peptides having anti-hypertensive and cholesterol-lowering effects in mammals and related nutritional and therapeutic products.

BACKGROUND

Coronary heart disease (CHD), which is considered the most common and serious form of cardiovascular disease, is the first cause of death in developed industrialized countries. Hypertension and elevated blood cholesterol levels, particularly high low density-density lipoprotein cholesterol (LDL-C), are two of the major modified risk factors for the development of CHD (Department of Health and Human Services, 2000).

The long-term regulation of blood pressure is associated with the rennin-angiotensin system. The conversion of angiotensin I into angiotensin II, a potent vasoconstrictor octapeptide, by the angiotensin-converting enzyme (ACE) [EC 3.4.15.1] has long been known. Hence, the inhibition of this enzyme can reduce high arterial blood pressure through ACE-inhibitory (ACEI) compounds. However, several side effects have been associated with the ACE-inhibitory drugs. On the other hand, ACEI peptides derived from foods sources such as milk proteins are considered safer and without the side effects associated with the drugs.

Milk proteins have received increased attention as potential ingredients in health-promoting functional foods. It is accepted that proteins from milk may act as precursors of biologically active peptides with different physiological effects on the digestive, endocrine, cardiovascular, immune and nervous systems (Korhonen, 2009, J. Funct. Foods 1: 177-187). Indeed, it has been reported that an effective way to increase the amount of bioactive peptides in dairy products is by milk fermentation with highly proteolytic strains of lactic acid bacteria (LAB) (López-Fandiño et al., 2006, Int. Dairy J. 16: 1277-1293). LAB growth in milk is dependent on the specific proteolytic systems for the generation of free peptides as a source of nitrogen (Hugenholtz, 2008, Int. Dairy J. 18, 466-475). Indeed, several ACEI peptides and/or with antihypertensive activity derived from milk proteins by the action of *Lactobacillus helveticus* and *Saccharomyces cerevisae* (Nakamura et al., 1995, J. Dairy Sci. 78:777-783; Nakamura et al., 1995, J. Dairy Sci. 78:1253-1257) or *Lactobacillus helveticus* (Sipola et al, 2002, J. Dairy Res. 69: 103-111; Seppo et al., 2003, Am. J. Clin. Nutr. 77:326-330) have been found. As a result, there are some commercial products, such as Calpis sour milk drink (Calpis Co., Japan) and Evolus (Valio, Finland). Calpis sour milk is claimed as suitable for those with mild hypertension and is fermented with *Lactobacillus helveticus* and *Saccharomyces cervisiae* and Evolus which is claimed as the first European functional food to help lower blood pressure, also fermented with *Lactobacillus helveticus*. Both fermented milk products contain bioactive peptides responsible for the ACE-inhibition and presented antihypertensive effects in hypertensive rats.

These biological effects of *Lactobacillus helveticus* strains have been described in the prior art. For instance, international patent application WO99/16862, Yamamoto et al., describes the strain *Lactobacillus helveticus* CM4, FERM BP-6060 which is capable of producing a large amount of the tripeptide Val-Pro-Pro and/or Ile-Pro-Pro. Furthermore, U.S. Pat. No. 5,449,661, Nakamura et al., describes the preparation of a peptide containing the tripeptide sequence Val-Pro-Pro and its use for lowering hypertension, obtained from fermenting milk with the strain *Lactobacillus helveticus* JCM 1004.

Similarly, it has been shown that peptides released by *Enterococcus faecalis* strains from milk proteins were able to decrease arterial blood pressure in spontaneously hypertensive rats (SHR) (Muguerza et al., 2006, Int. Dairy J., 16:61-69; Quirós et al., 2007, Int. Dairy J., 17, 33-41). In fact, international patent application WO 2004/104182, relates to *Enterococcus faecalis* bacteria which can produce bioactive peptides, such as peptides with ACE inhibitory activity and/or antihypertensive activity. Even though LAB and the specific species *Lactobacillus* and *Enterocoeccus*, have been widely studied and recommended for use for the production of health-promoting peptides, there is still constant pursuit of finding new bacteria which are useful for the production of bioactive peptides from dairy proteins. To the best of our knowledge, the beneficial health effects of peptides in fermented milk with *Lactococcus lactis* strains have not been reported. *L. lactis* is one of the most important LAB, since it generally takes part of commercial starter cultures used in the manufacture of fermented dairy foods (Odamaki et al., 2011, *Systematic Appl Microbiol* 34, 429-434). *Lactococcus lactis* strains are able to improve the organoleptic characteristics of dairy products since they are responsible for the formation of aromatic compounds (Ayad 2009, Food Microbiol 26, 533-541). Previous studies in our laboratory showed that specific *L. lactis* strains isolated from native ecosystems were able to produce remarkable aroma profiles in fermented milk (Gutierrez-Méndez et al., 2008, J. Dairy Sci. 91, 49-579). Furthermore, it was reported that a wild *L. lactis* strain presented ACEI peptides in Mexican Fresco cheese (Torres-Llanez, et al., 2011, J. Dairy Sci., 94: 3794-3800). Also, specific wild *L. lactis* strains were explored for their ability to produce ACEI activity in fermented milk (Rodríguez-Figueroa et al., 2010, J. Dairy Sci., 93: 5032-5038; Otte et al., 2011, Int. Dairy J., 21: 229-238). However, fermented milk products produced by *L. lactis* strains were not tested in vivo to show any health benefits.

Therefore, there is still a great demand for finding new effective microbes which are useful both as starters in fermented dairy foods and for the production of bioactive peptides with unique health benefits.

SUMMARY

Specific *Lactococcus lactis* strains NRRL B-50571 and NRRL B-50572 have the capacity to produce bioactive peptides that have remarkable capacity to generate an antihypertensive effect in mammals. Such hypotensive peptides do not change arterial blood pressure in subjects with normotensive arterial blood pressure; only hypertensive subjects experiment a reduction in arterial blood pressure. The bioactive peptides are a viable option to reduce arterial blood pressure without the secondary effects commonly produced by synthetic drugs.

Additionally, such bioactive peptides improve cardiovascular health by lowering bad (LDL) cholesterol and present antioxidant properties. Therefore, the mentioned lactic acid bacteria and the bioactive peptides included in this invention may be used in pharmaceutical preparations as well as in food products, such as functional foods.

One or more embodiments include the generation of bioactive peptides by the action of novel *Lactococcus lactis* NRRL B-50571 or NRRL B-50572 on a substrate comprising one or more proteins or its fragments, which contain specific amino acid sequences. These peptides could be used in an edible product such as a food product, food supplement or as a pharmaceutical composition.

One or more embodiments involve the manufacture of food products with bioactive peptides as a consequence of the action of specific *Lactococcus lactis* NRRL B-50571 and/or NRRL B-50572; or bacterial preparation of the bioactive peptides, with or without other microorganisms, on a substrate within the food. Also, these bioactive peptides may be separately produced and added to the food product, food supplement or pharmaceutical preparation as part of the formulation, with the purpose of reducing blood pressure, lowering LDL-cholesterol (bad cholesterol) and reducing oxidation, for better cardiovascular health.

DETAILED DESCRIPTION

Figure 1A:
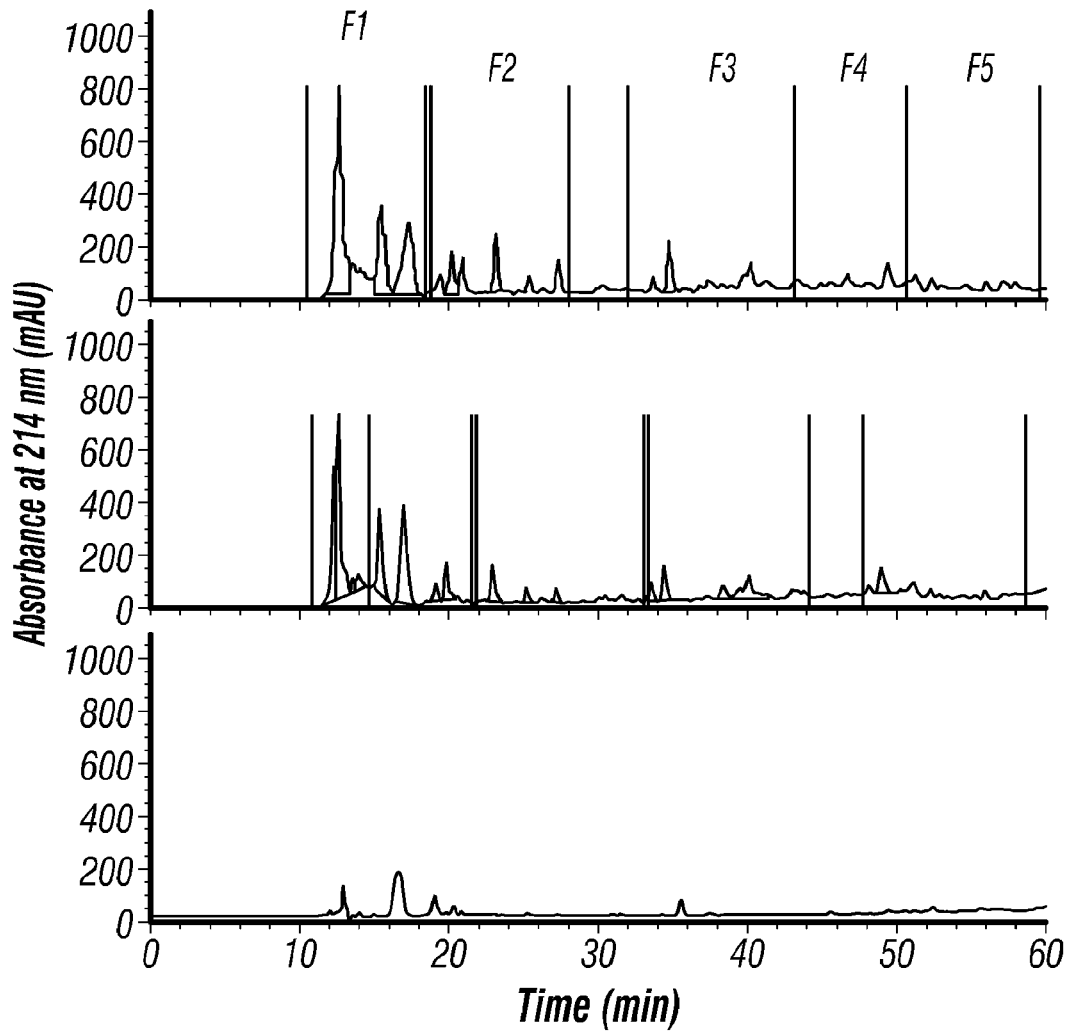
FIGS. 1A and 1B are diagrams showing typical RP-HPLC peptide profiles corresponding to water soluble extracts (WSE)<3 kDa fractions obtained from the fermentation of milk by specific wild *L. lactis* strains (NRRL B-50571 and NRRL B-50572) at 1A) 214 nm, 1B) 280 nm. C=unfermented milk.

The following abbreviations are used throughout the present application:
L. lactis—*Lactococcus lactis*;
ACE—angiotensin I-converting enzyme;
WSE—water soluble extract;
RP-HPLC—reverse phase high performance liquid chromatography;
MS—mass spectrometry;
SHR—spontaneously hypertensive rats;
BW—body weight;
SBP—systolic blood pressure;
DBP—diastolic blood pressure;
HR—heart rate;
PP—pulse pressure;
PWV—pulse wave velocity;
LAB—Lactic acid bacteria;
cfu—colony-forming units;
LSD—Least significant difference;
SEM—mean standard error;
NRRL B-50571-3—milk fermented by *L. lactis* NRRL B-50571 (35 mg protein/kg body weight (BW);

NRRL B-50572-3—milk fermented by *L. lactis* NRRL B-50572 (35 mg protein/kg BW);
NRRL B-50571-5—milk fermented by *L. lactis* NRRL B-50571 (50 mg protein/kg BW);
NRRL B-50572-5—milk fermented by *L. lactis* NRRL B-50572 (50 mg protein/kg BW);
ND—not detected; and
Vs—versus.

Specific *Lactococcus lactis* strains NRRL B-50571 and NRRL B-50572 have the ability to produce certain bioactive peptides having a remarkable capacity for generating an antihypertensive effect in mammals. These novel strains of *Lactococcus lactis* were deposited at the National Center for Agricultural Utilization Research, United States Department of Agriculture, 1815 N. University Street, Peoria, Ill. 61604, United States of America, on Sep. 17, 2011, which are *Lactococcus lactis* NRRL B-50571 and NRRL B-50572. These bacteria were isolated from raw milk products and were Gram positive, catalase negative and coccal-shaped organisms. These bacteria were identified as *Lactococcus lactis* by PCR amplification of the gene acmA (Buist et al., 1995, J. Bacteriol. 177:1554-1563) with the primers PALA 4 y PALA 14 (Table 1). Strains showed the classical characteristics for *Lactococcus*, such as positive growth at 10 C and 4% NaCl, but lack of growth at 45 C and pH 9.6. They also presented important technological characteristics such as high proteolytic activity (8 h to coagulate litmus milk), and the ability to ferment citrate, glucose, lactose and salicin in media. Similarly, when these strains were inoculated in reconstituted nonfat dry milk, they presented high acidifying activity (4.0<pH<5.0 in 24 h) and highproteolytic activity (Abs 340>0.10 in 24 h) according to the OPA (o-phtaldialdehyde method) (Church et al., 1983, J. Dairy Sci. 66:1219-1227).

The bacterial strains *Lactococcus lactis* NRRL B-50571 or NRRL B-50572 were propagated in 10 mL of sterile lactose (5 g $L^{-1}$) M17 broth and incubated at 30° C. for 24 h. Fresh cultures were obtained by repeating the same procedure. Initial starter culture were prepared by allowing *L. lactis* strains to reach $10^6$-$10^7$ colony-forming units (cfu) $mL^{-1}$ as enumerated on M17 agar containing lactose (5 g $L^{-1}$).

Production of Fermented Milk Containing Bioactive Peptides

Reconstituted nonfat dry milk (10%, w/v) was sterilized at 100° C. for 20 min. A loop of *L. lactis* single pre-culture (7-8 log cfu $mL^{-1}$) of NRRL B-50571 or NRRL B-50572 was inoculated into sterilized milk. The inoculated milk was incubated for 12 h at 30° C. Then, cultures were added (3% v/v) to reconstituted nonfat dry sterilized milk to get the different fermented milk batches. Incubation was carried out at 30° C. and stopped at 24 to 48 h by pasteurization at 75° C. for 1 min.

Preparation of the Water-Soluble Extracts (WSE) from Fermented Milk

Fermented milk was centrifuged at 20,000×g for 10 min at 0° C. Then, supernatants were collected and ultra-filtered through 3 kDa cut-off membranes at 9,800×g for 6 min. Permeates were collected, filtered through a 0.45 μm disposable hydrophilic filter and frozen at −80° C. until analysis were done.

ACE Inhibitory Activity of WSE from Milk Fermented with *L. lactis* strains NRRL B-50571 or NRRL B-50572

Water soluble extracts (<3 KDa) obtained after fermenting milk with *L. lactis* strains NRRL B-50571 or NRRL B-50572 presented high ACEI activity (>80%) and low $IC_{50}$'s (<25 μg/mL). The $IC_{50}$ is the amount of peptide content required to inhibit ACE activity by 50%. The ACE inhibitory activity was assayed by the method of Cushman and Cheung (Cushman and Cheung, 1971, Biochem. Phamacol. 20:1637-1648). The Cushman/Cheung method is based on the liberation of hippuric acid from hippuryl-L-histidyl-L-Leucine, catalyzed by ACE. The ACE inhibiting percentage was calculated by the following equation: Inhibiting percentage=(A−B)/(A−C)×100%, where A is the absorbance at 228 nm of hippuric acid free of sample, B is the absorbance at 228 nm of hippuric acid with sample, and C is the absorbance at 228 nm of hippuric acid free of ACE and sample.

Antioxidant Activity of WSE from Milk Fermented with *L. lactis* Strains NRRL B-50571 or NRRL B-50572

Water soluble extracts (<3 KDa) obtained after fermenting milk with *L. lactis* strains NRRL B-50571 or NRRL B-50572 presented high TROLOX (F. HOFFMAN-LAROCHE, LTD, Basel, Switzerland) equivalent antioxidant capacity (TEAC) (>1500 μM) as determined by the ABTS method (Re et al., 1999, Free Radical Bio. Med. 26(9):1231-1237). Thus, fermented milk by these specific *L. lactis* strains present the additional physiological effects of reducing the detrimental effects of oxidation without the need for the use of natural antioxidants such as vitamin E or vitamin C, which are extremely fat or water soluble, so their applications are limited and cannot be maintained stable for long periods of time. On the other hand, the safety of synthetic antioxidants such as butylhydroxyanisol (BHA) and butylhydroxytoluene (BHT) has become questioned and they are oil soluble, thus not useful for their use in aqueous systems. Due to the importance in preventing oxidation in biological systems and to improve stability of food products subject to oxidation, the discovery of WSE obtained from the fermentation of milk with specific *L. lactis* strains with good antioxidant properties, provides a new alternative for new commercial functional fermented dairy foods.

Figure 1B:
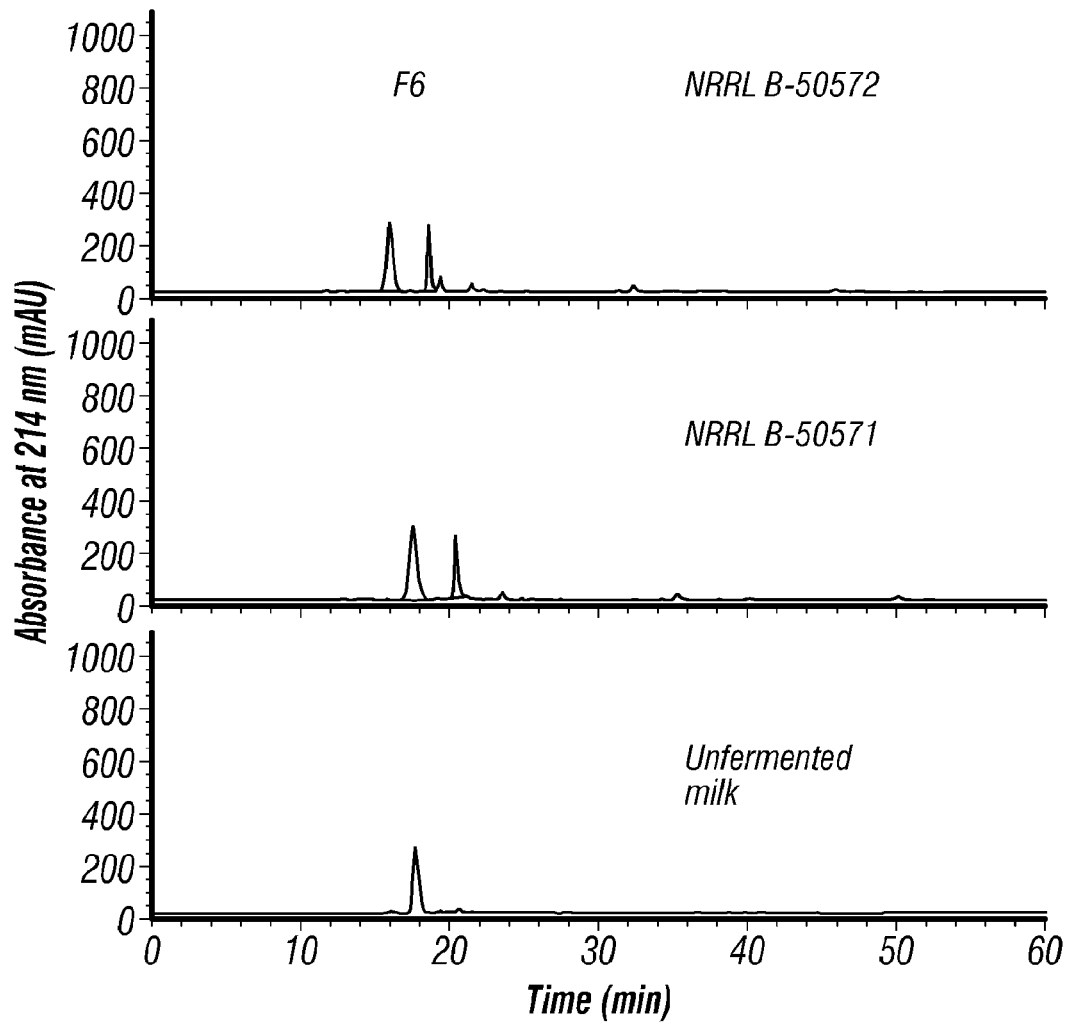
Figure 2:
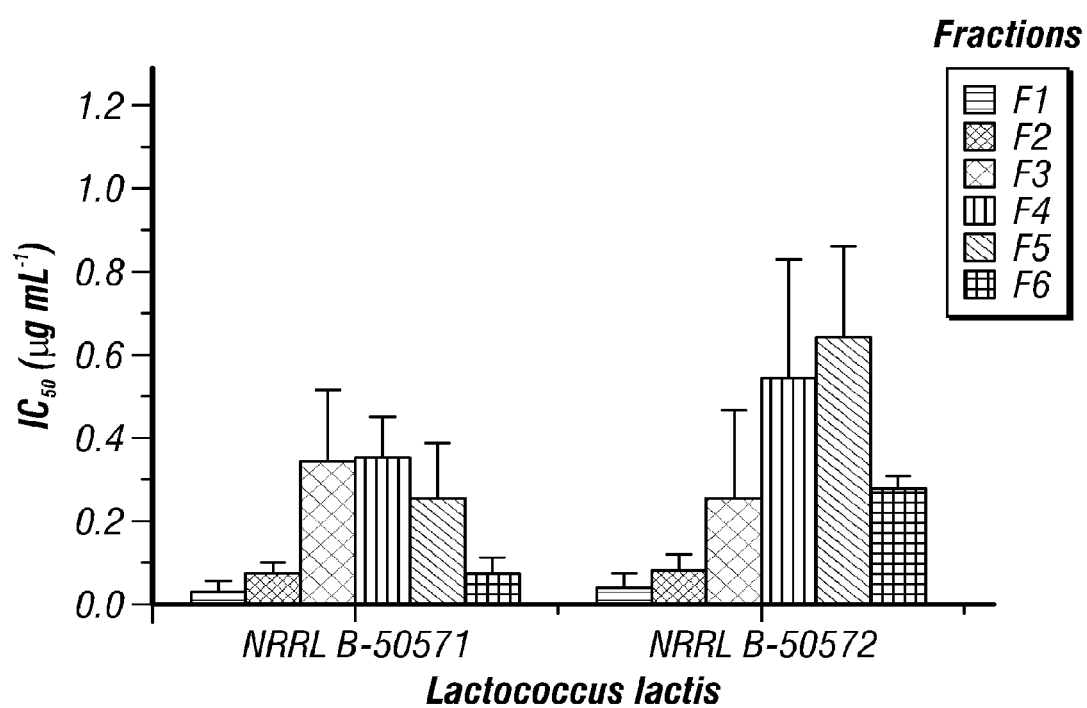
FIG. 2 presents $IC_{50}$ values of the peptide fractions obtained by hydrolysis of milk proteins with specific wild *L. lactis* strains obtained by RP-HPLC. Data represent mean values±SD (n=3). Statistical differences were considered with P<0.01, using one way ANOVA and Tukey-Kramer test. F=Peptide fraction. F1-F5=obtained at 214 nm; F6=obtained at 280 nm.

Isolation of ACEI Peptide Fractions by Reversed-Phase High-Performance Liquid Chromatography (RP-HPLC) and Identification by Tandem Mass Spectrometry Peptide profiles from WSE were obtained by RP-HPLC. Separation was carried out with a Discovery-$C_{18}$ (250 mm×4.6 mm, 5 μm particle size, 180 Å pore size) column from SUPELCO ANALYTICAL (Bellefonte, Pa., USA) with a solvent flow rate of 0.25 mL $min^{-1}$. Once the column was equilibrated with solvent A (0.04% Trifluoroacetic acid (TFA) in water), 20 μL of the WSE were injected. Peptides were eluted with an increasing gradient of solvent B (0.03% TFA in acetonitrile) from 0% to 45% in solvent A, during 60 min. Peptide profiles monitored at 214 nm and 280 nm were collected from five chromatographic runs and freeze-dried to be subjected to ACEI activity analysis and $IC_{50}$ determination (FIGS. 1 and 2). FIG. 1A shows WSE peptide fraction profiles produced by specific wild *L. lactis* strains monitored at 214 nm absorbance. Unfermented milk was used as a control. The area under the curve of each peptide profile was evaluated as an indirect measure of proteolysis. Results showed significant differences (P<0.01) between fermented milk peptide profiles and the control. On the other hand, the peptide profiles obtained from milk fermented with different strains of L. lactis were similar. The first peak eluted after 12 min in all samples. The largest concentration of peptides eluted between 12 and 25 min when the concentration of acetonitrile was between 9-13.5%, which may be related to the relatively hydrophobic nature of the eluted peptide. On the other hand, when WSE were monitored at 280 nm, only three peaks eluted between 16 and 20 min (FIG. 1B). These peptides may have ACEI activity since they were of aromatic nature.

Peptide chromatographic profiles were divided into 6 fractions and collected for further evaluation. Peptide profiles obtained at 214 nm were divided into F1-F5 fractions (FIG. 1A), meanwhile peptide profiles obtained at 280 nm corresponded to F6 (FIG. 1B). Peptide fractions F1-F6 showed remarkable $IC_{50}$ values ranging from 0.034±0.002 to 0.61±0.19 µg mL$^{-1}$ (FIG. 2). Results did not show significant difference (P>0.01) between all peptide fractions $IC_{50}$. However, the peptide fractions $IC_{50}$ values obtained from milk fermented by L. lactis strains NRRL B-50571 (0.076±0.004 and 0.034±0.002 µg mL$^{-1}$ for F1 and F6, respectively) and milk fermented by L. lactis NRRL B-50572 (0.041±0.003 and 0.084±0.003 µg mL$^{-1}$ for F1 and F2, respectively) showed the lowest values (FIG. 2). Therefore, the results suggest that the specific wild L. lactis strains presented have remarkable ACE-Inhibitory activity. Both strains did not present a significant difference (P>0.01) in $IC_{50}$ values and proteolysis, which are related to ACE-Inhibitory activity.

Figure 3A:
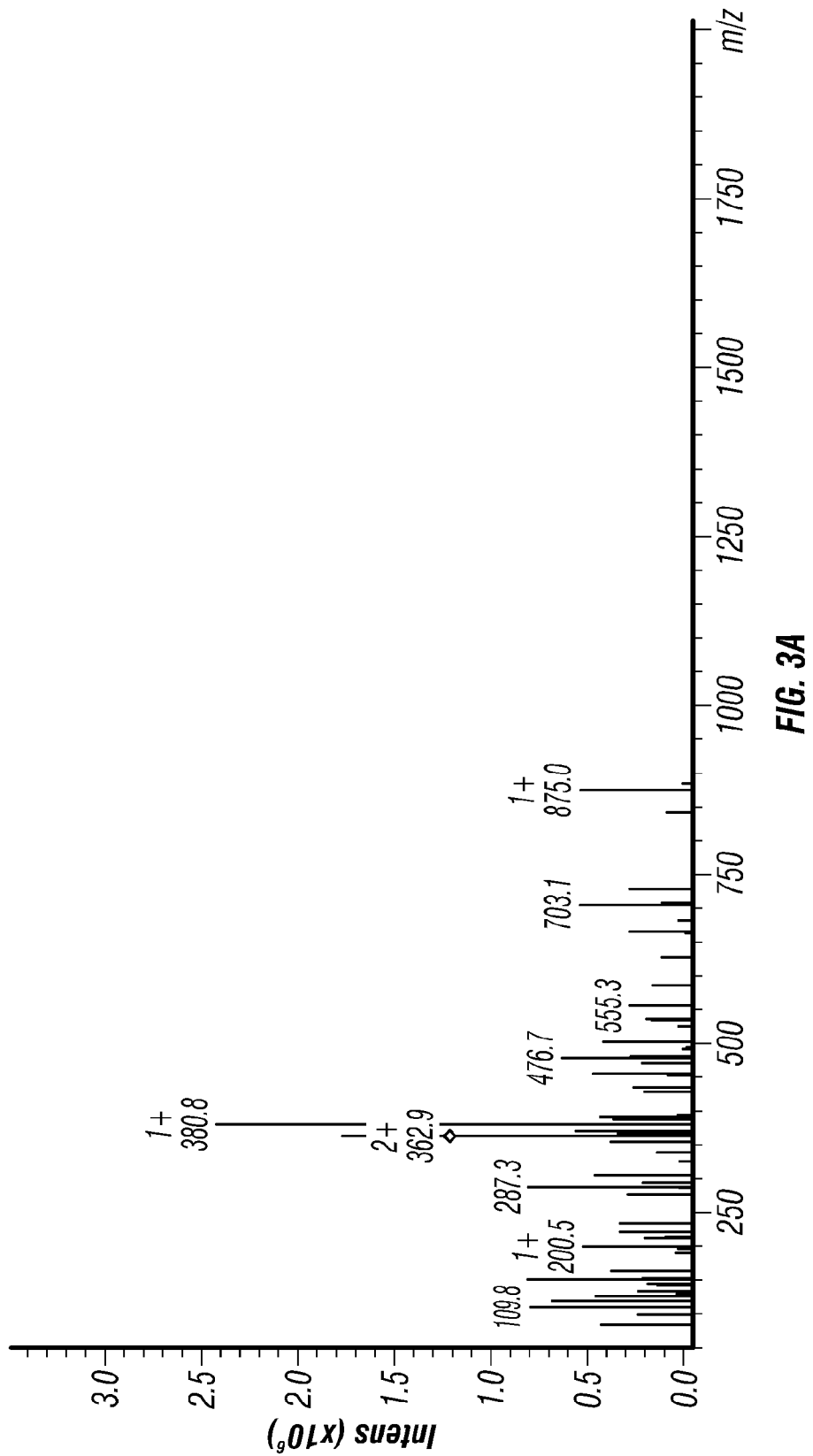
FIGS. 3A and 3B are typical mass spectra corresponding to a peptide sequence collected from the WSE F1 obtained from milk fermented by *L. lactis* NRRL B-50571: 3A) Double-charged ion 362.9 m/z.; 3B) MS/MS Spectrum for the specified ion in A). After interpretation and comparison in database, the fragment amino acid sequence matched with α-La (f63-68)
Figure 3B:
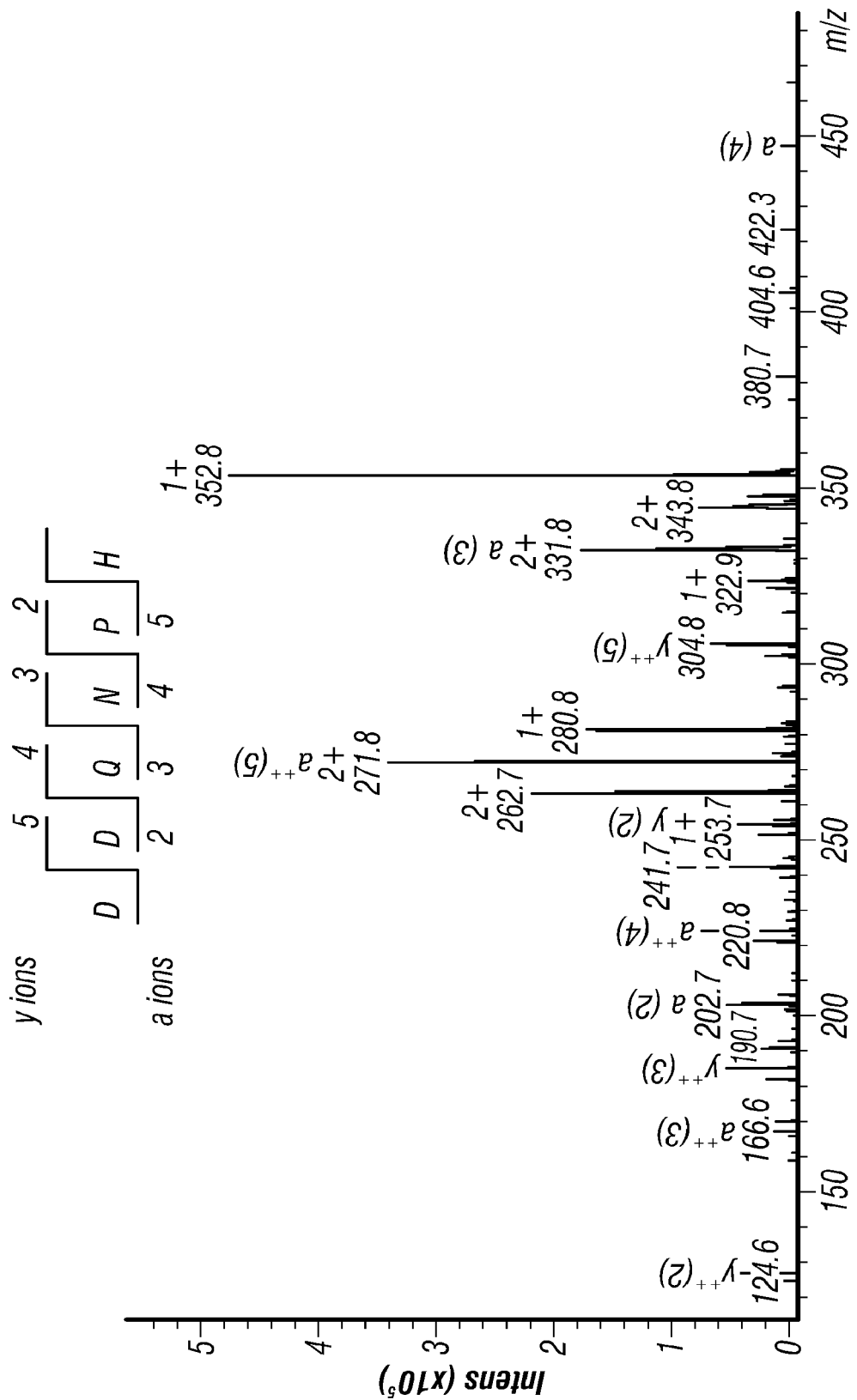

Peptide identification was performed by analyzing the different fractions by mass spectrometry using a 1100 Series LC/MSD Trap from Agilent equipped with an electro spray ionization source (LC-ESI-MS). The nano column was a $C_{18}$-300 (150 mm×0.75 µm, 3.5 µm; (AGILENT TECHNOLOGIES, INC., Palo Alto, Calif., USA). The sample injection volume was 1 µL. Solvent A was a mixture of water-acetonitrile-formic acid (10:90:0.1, v/v/v) and solvent B contained water-acetonitrile-formic acid (97:3:0.1, v/v/v). The gradient was based on the increment of solvent B which was initially set at 3% for 10 min and it took 23 more min to reach 65%. The 0.7 µL min$^{-1}$ flow rate was directed into the mass spectrometer via an electrospray interface. Nitrogen (99.99%) was used as the nebulizing and drying gas and operated with an estimated helium pressure of $5×10^{-3}$ bar. The needle voltage was set at 4 kV. Mass spectra were acquired over a range of 300-2500 mass/charge (m/z). The signal threshold to perform auto $MS^n$ analyses was 30,000. The precursor ions were isolated within a range of 4.0 m/z and fragmented with a voltage ramp from 0.35 to 1.1 V. Peptide sequences were obtained from mass spectrometry data using the Mascot server through the UniProtKB/Swissprot database sequences. Table 2 presents the identified sequences of peptides in the six fractions collected from milk fermented by specific L. lactis strains associated to ACEI activity. A typical mass spectrum of the peptide sequence DDQNPH, produced by L. lactis NRRL B-50571 fermented milk is shown in FIG. 3.

Antihypertensive Effects of Single-Dose Consumption of Milk Fermented by Specific Lactococcus lactis Strains NRRL B-50571 or NRRL B-50572

Previous work demonstrated that milk fermented by specific Lactococcus (L.) lactis strains significantly inhibited the activity of angiotensin I-converting enzyme (ACE). However, the relationship between ACEI and the in vivo action had to be tested. Therefore, the antihypertensive and heart rate (HR) lowering effect of milk fermented by specific L. lactis in a murine model was investigated. Spontaneously hypertensive male rats (SHR) (271±14 g) were randomized into four treatment groups: oral administration of milk fermented by L. lactis NRRL B-50571 or L. lactis NRRL B-50572 at 35 or 50 mg protein/kg of body weight (BW). Two more groups were fed with different solutions as controls: a saline solution was the negative control, meanwhile captopril (40 mg/kg BW), a proven ACE inhibitor was the positive control. Blood pressure and heart rate were monitored by the tail cuff method before treatments and 2, 4, 6 and 24 h post oral administration. Results demonstrated that milk fermented by L. lactis NRRL B-50571 as well as milk fermented by L. lactis NRRL B-50572 presented an important systolic (SBP) and diastolic blood pressure (DBP) and HR lowering effect. Thus, milk fermented by specific L. lactis strains present potential benefits in the prevention and treatment of cardiovascular diseases associated to hypertension in humans.

Samples of specific L. lactis fermented milk (prepared as previously described) for the single dose bioassay were obtained by centrifugation at 20,000×g for 10) min at 0° C. The supernatants were collected and lyophilized with a freeze dryer until used. The experimental protocol was performed with forty-two male spontaneously hypertensive male rats (SHR) (4-5 weeks old, 72±7 g body weight (BW)) obtained from HARLAN LABORATORIES, INC, (Indianapolis, Ind., USA). SHR were weaned for eight weeks and their systolic blood pressure monitored during this period. Rats were randomly housed in pairs per cage at 21±2° C. with 12 h light/dark cycles, 52±6% relative humidity and with ad libitum intake of a standard diet (TEKLAD, Harlan Laboratories, USA) and purified water. SHR (12-13 weeks old, 271±14 g BW) were divided into six groups of seven rats (n=7): Oral administration of saline was the negative control, meanwhile captopril (proven hypotensive drug) (40 mg/kg BW) was the positive control. Animals were weighed before oral administration in order to prepare the corresponding amount of lyophilized whey/kg of animal weight. Lyophilized whey fractions of milk fermented by L. lactis NRRL B-50572 or NRRL B-50571 were dissolved in 0.8 mL of saline. Treatments were NRRL B-50572-3 (35 mg protein/kg BW), NRRL B-50572-5 (50 mg protein/kg BW), NRRL B-50571-3 (35 mg protein/kg BW) and NRRL B-50571-5 (50 mg protein/kg BW).

Conscious SHR received a single dose through a cannula between 8:30 and 9:30 am to eliminate circadian cycles. Animals were restrained in the warming chamber for 20 min at 32° C. to detect pulsations through the caudal artery. Systolic blood pressure (SBP), diastolic blood pressure (DBP) as well as heart rate (HR) were monitored before administration and 2, 4, 6 and 24 h post-administration. Measurements were taken five times using the non-invasive blood pressure system included photoelectric sensor, amplifier, automatic inflation cuff and software (Model 229, IITC LIFE SCIENCE, Woodland Hills, Calif., USA). The animal experimental procedures were done following the guidelines and supervision of the CIAD (Centro de Investigación en Alimentación y Desarrollo), A.C. Committee of Ethics for scientific research.

Figure 4A:
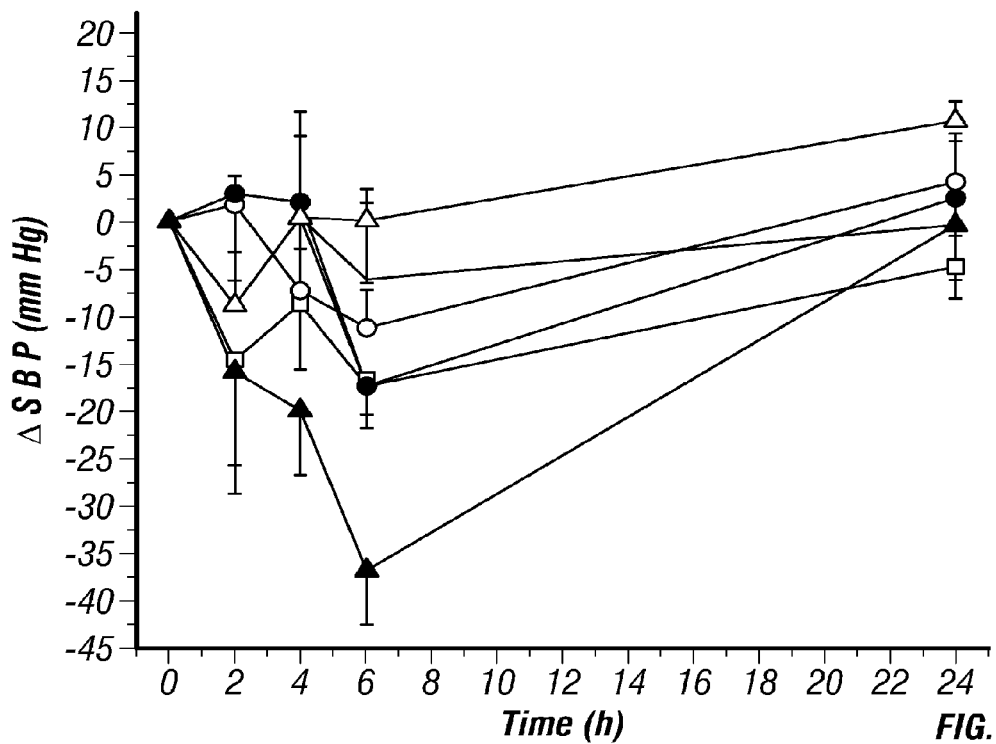
FIGS. 4A-4C are diagrams showing the change in blood pressure and HR during 24 h in SHR treated with milk fermented by specific *L. lactis* strains: (4A) systolic blood pressure (SBP), (4B) diastolic blood pressure (DBP) and (4C) heart rate (HR). Positive control captopril, negative control saline, whey fraction of milk fermented by *L. lactis* NRRL B-50572-3 (35 mg protein/kg BW), whey fraction of milk fermented by *L. lactis* NRRL B-50571-3 (35 mg protein/kg BW), whey fraction of milk fermented by *L. lactis* NRRL B-50572-5 (50 mg protein/kg BW), whey fraction of milk fermented by *L. lactis* NRRL B-50571-5 (50 mg protein/kg BW). Data is shown by means with their standard error. Each SHR group had seven animals.

SBP changes are shown in FIG. 4a. Results showed the maximal SBP reductions at 6 h post oral administration. SHR treated with the whey fractions of milk fermented by L. lactis NRRL B-50572-5 and L. lactis NRRL B-50571-3 presented the more relevant decrement of SBP, 16.7±3.5 mm Hg and 17.7±4.0 mm Hg, respectively, although treatments were not significantly different (P<0.05). The maximum decrease at 6 h was observed in animals treated with captopril which was significantly different from the treatments (P<0.05). However, the SBP measurements 24 h post administration showed that SHR treated with the whey fraction of milk fermented by *L. lactis* NRRL B-50572-5 presented 4.3 mm Hg less than rats that were treated with captopril. These results suggest that *L. lactis* NRRL B-50572-5 fermented milk may have an important residual blood pressure reducing effect. Moreover, a remarkable 15.3 mm Hg SBP decrement between SHR that received the whey fraction of milk fermented by *L. lactis* NRRL B-50572-5 and SHR treated with saline was found. Hence, blood pressure measurements suggested an absence of dosage dependent relationship between the protein content of the whey fraction corresponding to milk fermented by *L. lactis* NRRL B-50571 and its ability to reduce SBP, meanwhile the whey fraction of milk fermented with *L. lactis* NRRL B-50572 was dosage dependent.

Figure 4B:
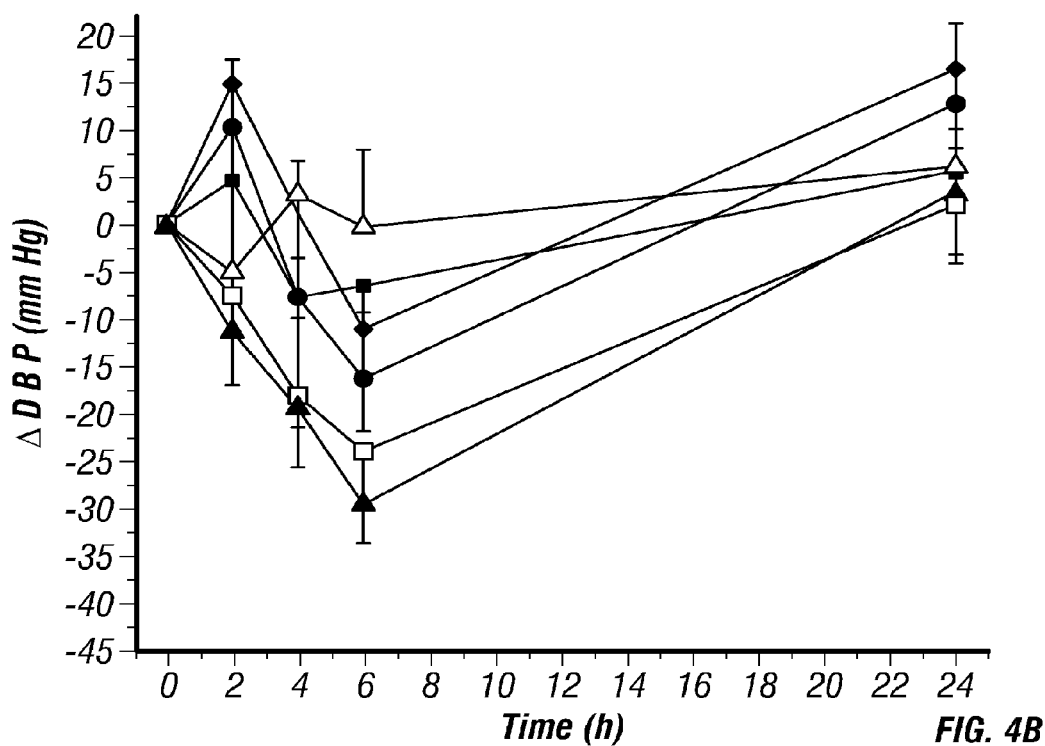

FIG. 4b shows the reduction of DBP in SHR caused by the oral administration of the whey fraction of milk fermented by specific *L. lactis* strains. The highest decrement of DBP was observed at 6 h post oral administration. At the same time, no significant difference was found (P<0.05) when SHR were treated with whey fraction of milk fermented by *L. lactis* NRRL B-50571 at any protein content or whey fraction of fermented milk *L. lactis* NRRL B-50572-5. Whey fractions from milk fermented by *L. lactis* NRRL B-50571 as well as milk fermented with *L. lactis* NRRL B-50572 presented an important dosage dependent antihypertensive effect through DBP measurements. Although, captopril generated the maximum DBP reduction with each measurement, there was not a significant difference (P<0.05) with the hypotensive effect of the whey fraction of milk fermented by *L. lactis* NRRL B-50572-5.

Figure 4C:
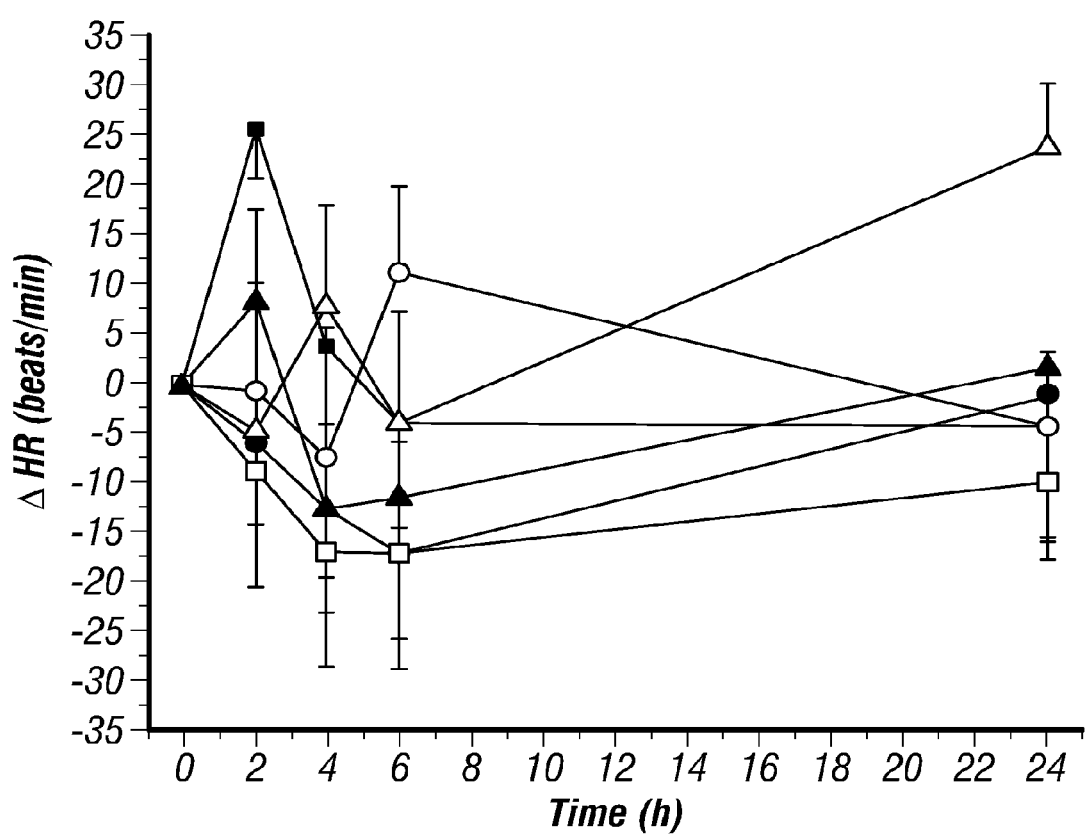

HR reductions at 2, 4, 6 and 24 h of treated SHR are shown in FIG. 4c. There was not a significant difference (P<0.05) in HR presented by rats administered with whey fractions from milk fermented with *L. lactis* NRRL B-50572-5 or NRRL B-50571-3 or captopril. As in SBP and DBP, the lowest HR values were found at 6 h post administration of treatments. In fact, SHR treated with the whey fraction *L. lactis* NRRL B-50571-3 fermented milk, as well as the whey fraction *L. lactis* NRRL B-50572-5 fermented milk presented the maximal HR decrement, 16.6±9.2 and 16.9±11.5 beats min$^{-1}$, respectively. Moreover, a significant (P<0.05) HR decrement (33.4 beats/min) was found in SHR that received the whey fraction from *L. lactis* NRRL B-50572-5 fermented milk when compared with saline treatment at the end of the 24-h post oral administration.

Antihypertensive and Hypolipidemic Effects of Long-Term Consumption of Milk Fermented by Specific *Lactococcus lactis* Strains NRRL B-50571 or NRRL B-50572

It was demonstrated that the fractions of these fermented milks, showed an acute antihypertensive and heart rate (HR)-lowering effect in spontaneously hypertensive rats after receiving a single dose. Thus, the antihypertensive and hypolipidemic effects of long-term consumption of fermented milk with specific *L. lactis* strains were also tested in SHR.

SHR were feed ad libitum with milk fermented by *L. lactis* NRRL B-50571, *L. lactis* NRRL B-50572, captopril (40 mg/kg body weight) or purified water for four weeks. Results suggested that *L. lactis* fermented milks presented a significant (p<0.05) blood pressure-lowering effect. There was not a significant difference (p>0.05) among milk fermented by *L. lactis* NRRL B-50571 and captopril by the second and third week of treatment. Additionally, milk fermented by *L. lactis* strains modified SHR lipid profiles. Milk fermented by *L. lactis* NRRL B-50571 and B-50572 was able to reduce plasma low-density lipoprotein (LDL) cholesterol by 55.4±3 mg/dL and 66.3±4 mg/dL, respectively. Thus, milk fermented by *L. lactis* strains may be a coadjuvant in the reduction of hypertension and hyperlipidemia and may be used as a functional food for better cardiovascular health.

Samples of specific *L. lactis* fermented milk (prepared as previously described) were prepared by heating at 98° C. for 10 min to inactive proteases and *L. lactis* strains. Subsequently, samples were frozen at −20° C. All fermented milk samples were daily unfrozen and homogenized (for 20 minutes before use. Thirty-two male SHR were obtained from Harlan Laboratories, Inc., (Indianapolis, Ill., USA). The rats were randomly housed in pairs per cage at 21±2° C. with 12 h light/dark cycles, 52±6% relative humidity and with ad libitum intake of a standard diet (TEKLAD, Harlan Laboratories, USA) during the experiment. SHR (27-28 weeks old and 355±24 g weight) were divided into four groups of eight rats (n=8): purified water (negative control), captopril (proven hypotensive drug, positive control) (40 mg/kg body weight (BW), milk fermented by *L. lactis* NRRL B-50571 and milk fermented by *L. lactis* NRRL 50572. All SHR had free access to each treatment during three weeks as part of the protocol. Half of the animals were sacrificed at the end of that period. The rest of the SHR only received purified water during one more week before being sacrificed. A research animal protocol was followed according to the guidelines established by the institutional (CIAD, A.C.) Ethics Committee. The lowering blood pressure effect of milk fermented by specific *L. lactis* strains on SHR was monitored through time. Animals were deposited in restrainers in the warming chamber for 20 min at 32° C. to detect pulsations through the caudal artery. Systolic (SBP) and diastolic (DBP) blood pressures were measured five times on each conscious animal before treatments and every week during the experiment. Measurements were obtained using the tail-cuff method between 9 and 12 h to eliminate circadian cycles. The non-invasive blood pressure system used in this experiment included a photoelectric sensor, an amplifier, an automatic inflation cuff and software (Model 229, IITC Life Science Inc., Woodland Hills, Calif., USA).

The hypolipidemic activity of milk fermented by specific *L. lactis* strains were also evaluated in SHR. Blood samples were collected under anesthesia by cardiac puncture in tubes with heparin (SARSTEDT AG & CO., Nümbrecht, Germany). Subsequently, samples were centrifuged at 2,500 rpm, 4° C. for 10 min to obtain the plasma and they were frozen at −20° C. for further studies. Triglycerides (TG), total cholesterol (TC), and high-density lipoprotein cholesterol (HDL-C) levels in plasma were determined by a commercial kit (RANDOX LABORATORIES, Kearneysville, W. Va., USA), while low density lipoprotein cholesterol (LDL-C) was calculated as the difference between TC and HDL-C according to specifications.

Figure 5:
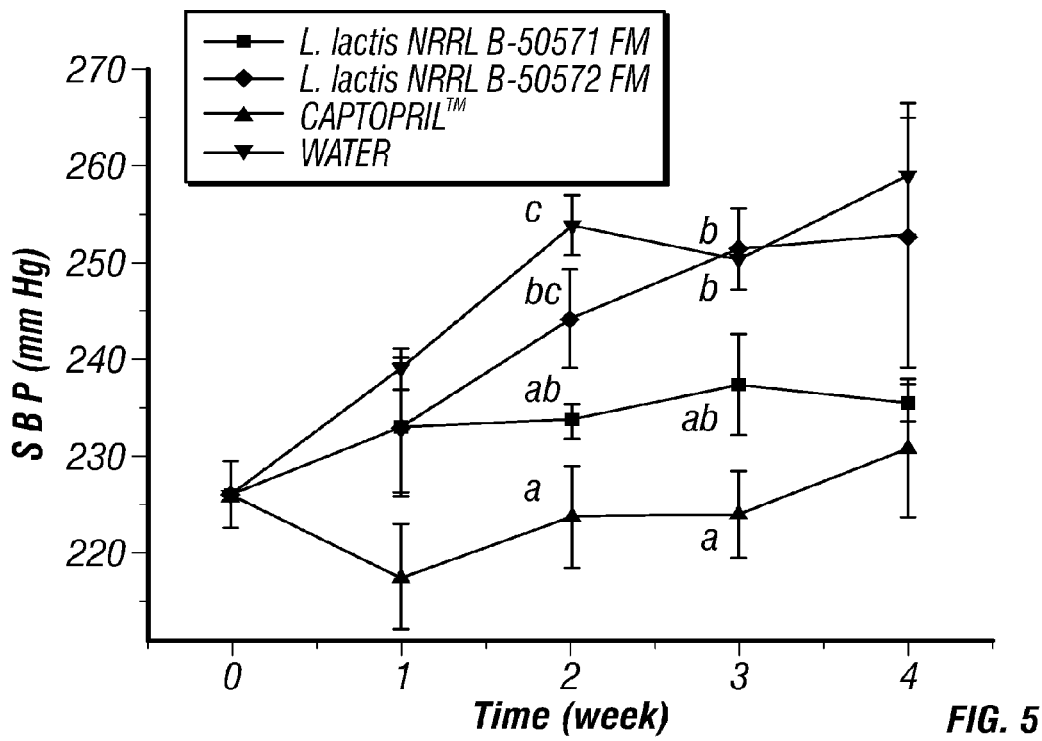
FIG. 5 is a diagram showing the change in systolic blood pressure during 4 weeks of SHR treated by *L. lactis* fermented milk. *L. lactis* NRRL B-50571 fermented milk; *L. lactis* NRRL B-50572 fermented milk; captopril=Positive control; Purified water=Negative control. Data is shown by mean values±SEM (n=8). FM=Fermented milk.
Figure 6:
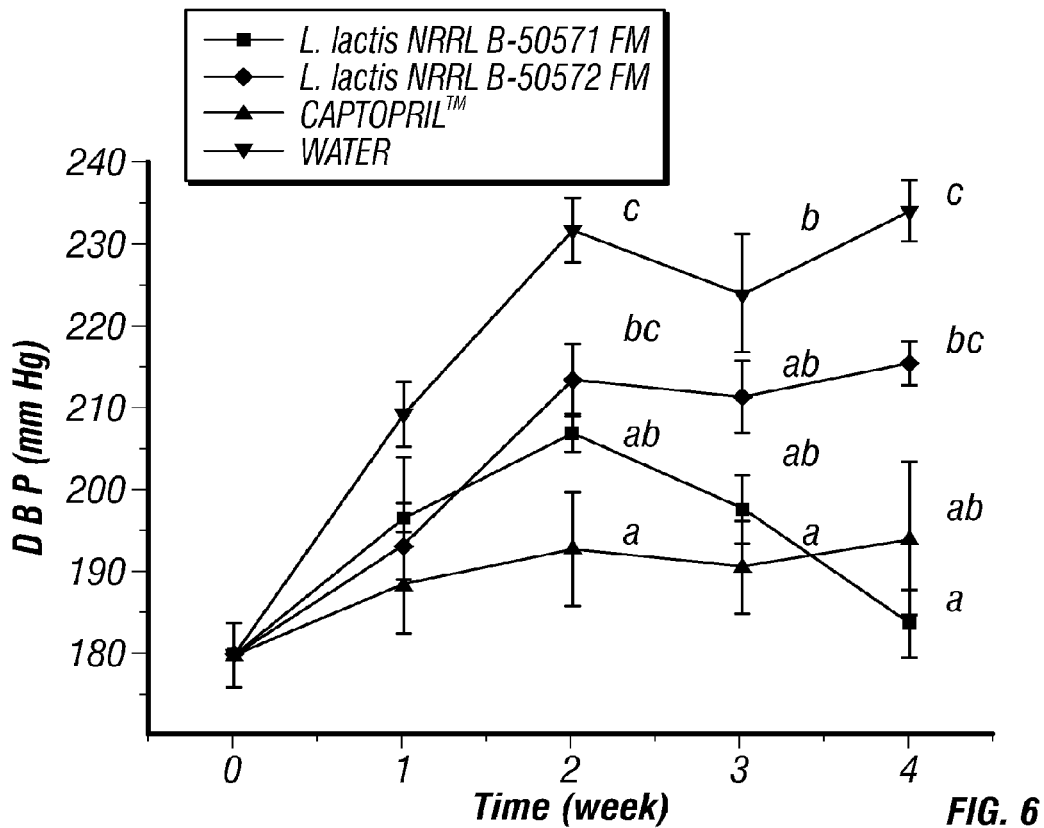
FIG. 6 is a diagram showing the diastolic blood pressure during 4 weeks of SHR treated by *L. lactis* fermented milk. *L. lactis* NRRL B-50571 fermented milk; *L. lactis* NRRL B-50572 fermented milk; captopril=Positive control; Purified water=Negative control. Data is shown by mean values±SEM (n=8). FM=Fermented milk.

Both *L. lactis* fermented milks were able to reduce blood pressure during the experiment (FIGS. 5 and 6). Results did not show significant difference (P>0.05) between systolic blood pressure (SBP) measurements in the first week (FIG. 5). However, by the second week, the SBP reduction in SHR that received milk fermented by *L. lactis* NRRL B-50571 (−20.2±3.8 mm Hg) was not statistically different (P>0.05) from those that received captopril (−30.1±7.1 mm Hg). In fact, by the second and third week, SHR treated with captopril or milks fermented by *L. lactis* NRRL B-50571 or B-50572 presented a marked lowering-effect on SBP. By the fourth week of treatment, milk fermented by *L. lactis* NRRL B-50571 was able to reduce SBP by 23.3±1.8 mm Hg, meanwhile captopril reduced SBP by 28.1±1.8 mm Hg As it is observed in FIG. 5, the SBP lowering-effect in SHR treated with milk fermented by *L. lactis* NRRL B-50571 increases with time. Indeed, the maximal SBP reduction was found by the fourth week, even though animals drank only water in the last week. Thus, these results suggest a residual SBP lowering-effect after cessation of the treatment. Milk fermented containing antihypertensive peptides administered for long periods may extend their bioactivity even after cessation of the treatment.

SHR treated with milk fermented by *L. lactis* NRRL B-50571 and B-50572 presented DBP lowering-effect during the experiment (FIG. 6). As in SBP, the first week, DBP measurements were not significantly different (P>0.05) between treatments. However, by the second week, milk fermented by *L. lactis* NRRL B-50571 was able to reduce DBP by 24.5±6.6 mm Hg. Meanwhile, captopril reduced DBP by 38.4±8.5 mm Hg. Furthermore, by the third experimental week, the DBP lowering-effect was not significantly different (P>0.05) between SHR treated with captopril and milk fermented by *L. lactis* NRRL B-50571 or B-50572. The most important DBP reduction (49.8±3.5 mm Hg) was observed by the fourth week of treatment in SHR that received milk fermented by *L. lactis* NRRL B-50571.

Figure 7:
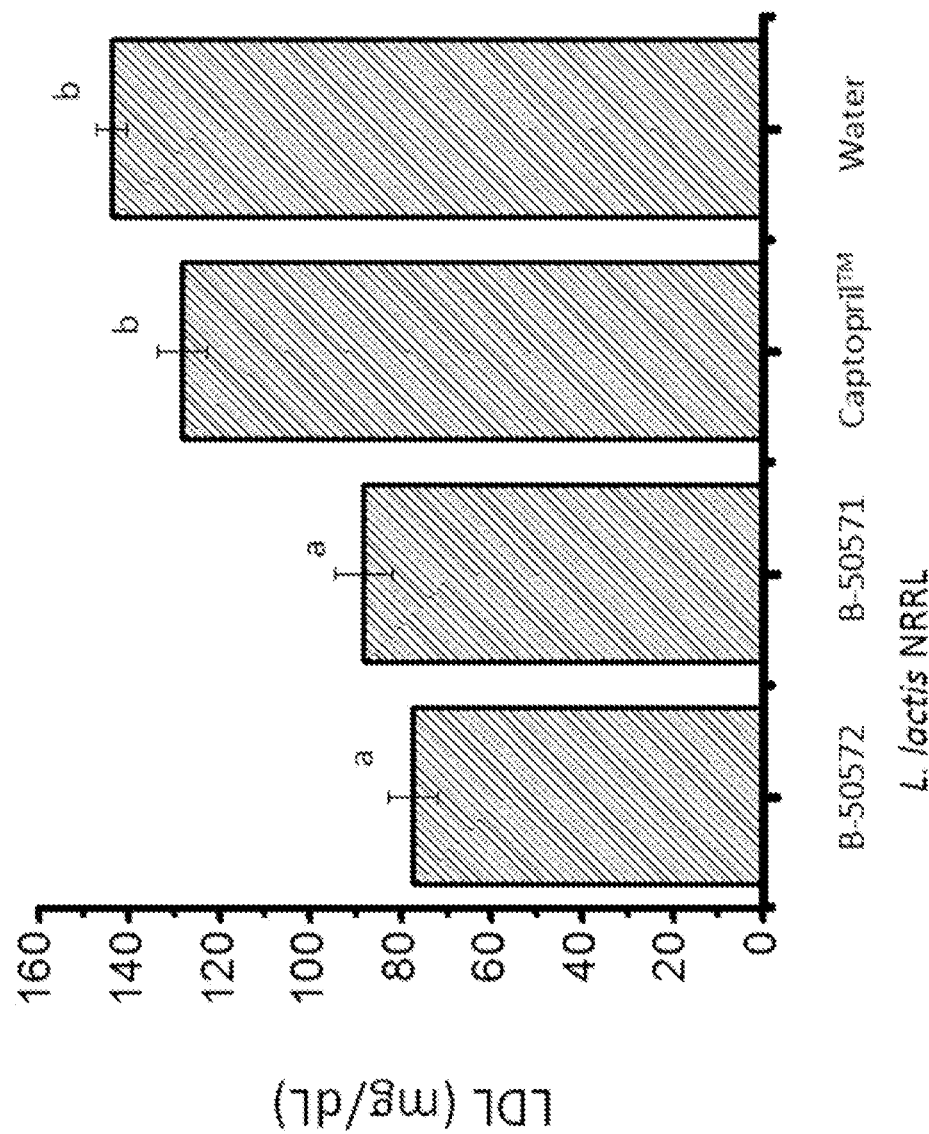
FIG. 7 is a diagram showing plasma low-density lipoprotein cholesterol in SHR treated by *L. lactis* fermented milk for 4 weeks. Captopril=Positive control; Purified water=Negative control. Data is shown by mean values±SEM (n=8)
Figure 8:
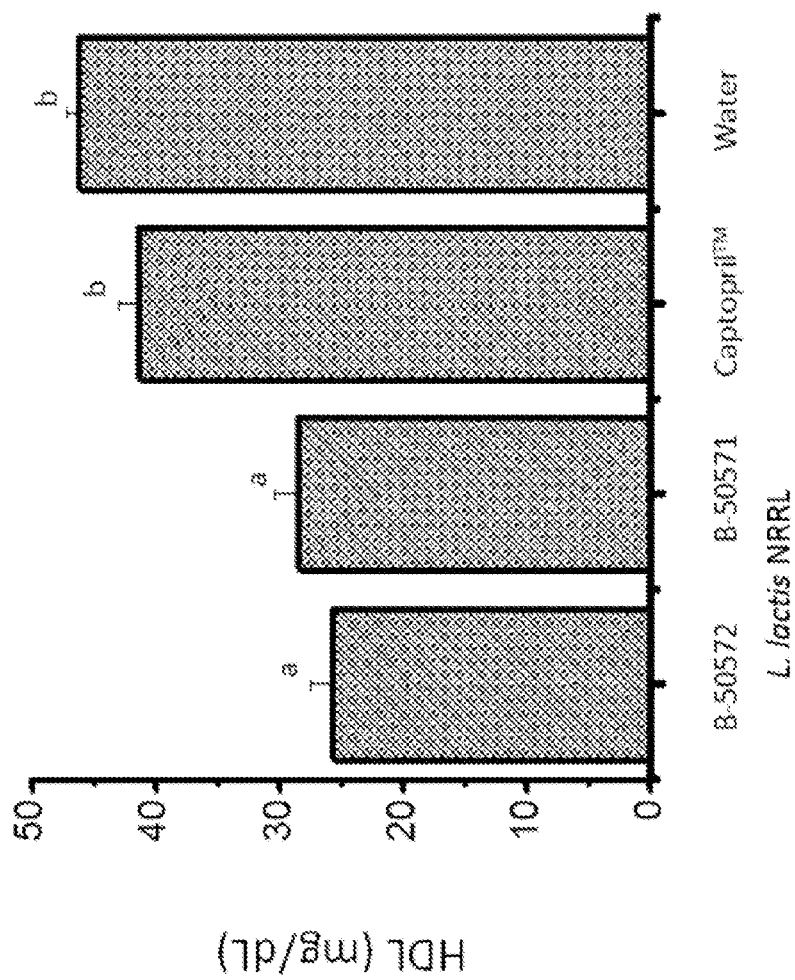
FIG. 8 is a diagram showing plasma high-density lipoprotein cholesterol in SHR treated by *L. lactis* fermented milk for 4 weeks. Captopril=Positive control; Purified water=Negative control. Data is shown by mean values±SEM (n=8)

In addition, fermented milks were able to modify SHR lipid profiles by the third week of treatment. SHR that received milk fermented by *L. lactis* NRRL B-50571 or B-50572 presented 55.4±3 mg/dL and 66.2±4 mg/dL reduction of low-density lipoprotein cholesterol (LDL-C), respectively, when compared to SHR administered purified water (FIG. 7). Similarly, results showed that milk fermented by *L. lactis* strains reduced HDL-C significantly (P<0.05) in treated SHR (FIG. 8).

Figure 9:
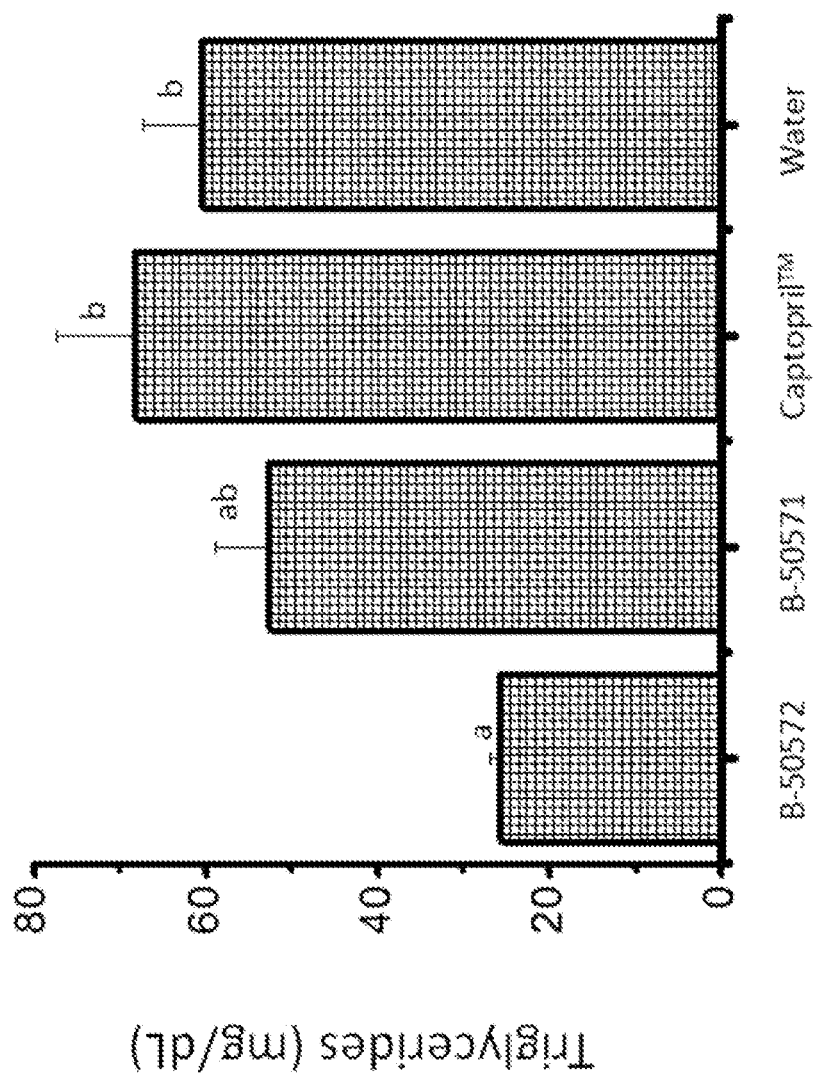
FIG. 9 is a diagram showing plasma triglycerides in SHR treated by *L. lactis* fermented milk for 4 weeks. Captopril=Positive control; Purified water=Negative control. Data is shown by mean values±SEM (n=8)
Figure 10:
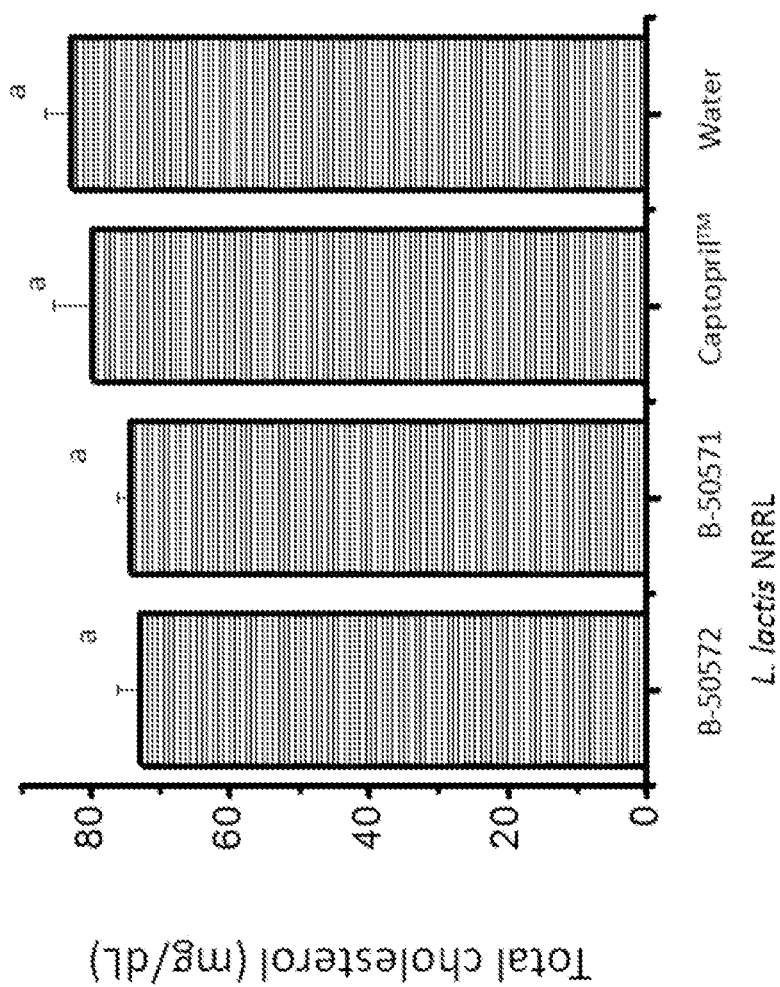
FIG. 10 is a diagram showing plasma total cholesterol in SHR treated by *L. lactis* fermented milk for 4 weeks. Captopril=Positive control; Purified water=Negative control. Data is shown by mean values±SEM (n=8)

Plasma triglyceride (TG) content was also decreased by 34.7±3.7 mg/dL in SHR treated with *L. lactis* NRRL B-50572 fermented milk when compared to purified water (FIG. 9). Additionally, plasma total cholesterol (TC) content was also reduced in treated SHR, although differences were not significantly different. Milk fermented by *L. lactis* NRRL B-50572 or B-50571 was able to reduce TC by 10±3.2 mg/dL and 8.6±2.4 mg/dL, respectively (FIG. 10).

The cholesterol lowering effect may be attributed to cholesterol removal by the *L. lactis* strains per se, however, this remains to be determined. On the other hand, the lowering effect on LDL-C observed in this study may also be attributed to the ingestion by SHR of dairy protein and/or peptides produced by *L. lactis*, including those from whey protein.

The use of milk fermented by specific lactic acid bacteria may be considered as a coadjuvant for the improvement of cardiovascular health. To the best of our knowledge, this is the first in vivo study that showed the antihypertensive and hypolipidemic effects of long-term consumption of fermented milk with specific *L. lactis* strains. Thus, dairy products fermented with *L. lactis* strains, NRRL B-50571 and NRRL B-50572 may be used as functional foods with potential benefits for cardiovascular health.

TABLE 1

Primers used for the identification of *Lactococcus lactis* strains

| Primer | Sequence |
| --- | --- |
| PALA 4 | (5'-CTTCAACAGACAAGTCC-3'), SEQ ID NO: 22 |
| PALA 14 | (5'-GATAAATGATTCCAAGC-3'), SEQ ID NO: 23 |

TABLE 2

Identification of peptides sequences obtained from milk fermented by specific wild *L. lactis* strains associated to ACEI activity.

| Sample[a] | Experimental Mass | Theoretical Mass | Sequence ID. | Protein fragment | Sequence |
| --- | --- | --- | --- | --- | --- |
| NRRL B-50571 | 723.9 | 724.3 | 1 | α-La (f63-68) | DDQNPH |
|  | 1032.8 | 1033.5 | 2 | α-La (f82-89) | LDDDLTDDI |
| F1 | 698.6 | 698.3 | 3 | κ-CN (f35-40) | YPSYGL |
|  | 1479.0 | 1479.7 | 4 | κ-CN (f98-110) | HPHPHLSFMAIPP |
|  | 1035.7 | 1035.5 | 5 | α-La (f55-62) | YDTQAIVQ |
|  | 1386.8 | 1387.7 | 6 | α-La (f100-111) | DDDLTDDIMCV |
|  | 585.9 | 585.2 | 7 | κ-CN (f35-39) | YPSYG |
| F2 | 505.9 | 585.2 | 8 | $α_{S1}$-CN (f62-66) | AESIS |
| F3 | 830.1 | 830.5 | 9 | β-CN (f22-28) | SITRINK |
|  | 1051.4 | 1051.5 | 10 | $α_{S1}$-CN (f80-88) | HIQKEDVPS |
|  | 904.1 | 904.5 | 11 | κ-CN (f161-169) | TVQVTSTAV |
| F4 | 904.3 | 904.5 | 11 | κ-CN (f161-169) | TVQVTSTAV |
|  | 1038.4 | 1038.6 | 12 | $α_{S2}$-CN (f115-124) | NAVPITPTLN |
|  | 977.1 | 977.6 | 13 | β-CN (f69-77) | SLPQNIPPL |
| F5 | 1716.9 | 1717.0 | 14 | β-CN (f194-209) | QEPVLGPVRGPFPIIV |
|  | 1150.4 | 1150.7 | 15 | β-CN (f199-209) | GPVRGPFPIIV |
|  | 977.2 | 977.6 | 13 | β-CN (f69-77) | SLPQNIPPL |
|  | 1094.4 | 1094.6 | 16 | κ-CN (f25-33) | YIPIQYVLS |

TABLE 2 -continued

Identification of peptides sequences obtained from milk fermented by specific wild *L. lactis* strains associated to ACEI activity.

| Sample[a] | Experimental Mass | Theoretical Mass | Sequence ID. | Protein fragment | Sequence |
|---|---|---|---|---|---|
| F6 | 904.4 | 904.5 | 11 | κ-CN (f161-169) | TVQVTSTAV |
|  | 1356.7 | 1357.7 | 17 | κ-CN (f157-169) | PEINTVQVTSTAV |
|  | 591.8 | 592.3 | 18 | Serotransferrin (f448-453) | GYLAVA |
| NRRL B-50572 | 1371.53 | 1372.7 | 19 | β-CN (f129-140) | DVENLHLPLPLL |
|  | 698.6 | 698.3 | 3 | β-CN (f35-40) | YPSYGL |
| F1 | 549.8 | 550.2 | 20 | β-Lg (f60-64) | ENGEC |
| F2 | 904.2 | 904.5 | 11 | κ-CN (f161-169) | TVQVTSTAV |
| F3 | 904.2 | 904.5 | 11 | κ-CN (f161-169) | TVQVTSTAV |
| F5 | 1150.5 | 1150.7 | 15 | β-CN (f199-209) | GPVRGPFPIIV |
| F6 | 922.4 | 922.4 | 21 | α-La (f86-93) | TDDIMCVK |

[a] = Fractions collected from milk fermented by *L. lactis* NRRL B-50571 and NRRL B-50572.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

The invention claimed is:

1. A bacterial preparation comprising a combination of biologically pure cultures of *Lactococcus lactis* strains NRRL B-50571 and NRRL B-50572.

2. A milk or milk-based product, which has been heat-processed and then inoculated with the bacterial preparation of claim 1.

3. An edible product prepared by fermenting a milk or milk-based starting material with the bacterial preparation of claim 1 and removing unhydrolyzed protein.

4. A milk or milk-based product, which has been heat-processed and then inoculated with *Lactococcus lactis* strain NRRL B-50571.

5. An edible product prepared by fermenting a milk or milk-based starting material with *Lactococcus lactis* strain NRRL B-50571 and removing unhydrolyzed protein.

* * * * *

SEQUENCE LISTING

```
<160> NUMBER OF SEQ ID NOS: 23

<210> SEQ ID NO 1
<211> LENGTH: 6
<212> TYPE: PRT
<213> ORGANISM: L. lactis NRRL B-50571

<400> SEQUENCE: 1

Asp Asp Gln Asn Pro His
1               5

<210> SEQ ID NO 2
<211> LENGTH: 9
<212> TYPE: PRT
<213> ORGANISM: L. lactis NRRL B-50571

<400> SEQUENCE: 2

Leu Asp Asp Asp Leu Thr Asp Asp Ile
1               5

<210> SEQ ID NO 3
<211> LENGTH: 6
<212> TYPE: PRT
<213> ORGANISM: L. lactis NRRL B-50571

<400> SEQUENCE: 3

Tyr Pro Ser Tyr Gly Leu
1               5

<210> SEQ ID NO 4
<211> LENGTH: 13
<212> TYPE: PRT
<213> ORGANISM: L. lactis NRRL B-50571
```

```
<400> SEQUENCE: 4

His Pro His Pro His Leu Ser Phe Met Ala Ile Pro Pro
1               5                   10

<210> SEQ ID NO 5
<211> LENGTH: 8
<212> TYPE: PRT
<213> ORGANISM: L. lactis NRRL B-50571

<400> SEQUENCE: 5

Tyr Asp Thr Gln Ala Ile Val Gln
1               5

<210> SEQ ID NO 6
<211> LENGTH: 11
<212> TYPE: PRT
<213> ORGANISM: L. lactis NRRL B-50571

<400> SEQUENCE: 6

Asp Asp Asp Leu Thr Asp Asp Ile Met Cys Val
1               5                   10

<210> SEQ ID NO 7
<211> LENGTH: 5
<212> TYPE: PRT
<213> ORGANISM: L. lactis NRRL B-50571

<400> SEQUENCE: 7

Tyr Pro Ser Tyr Gly
1               5

<210> SEQ ID NO 8
<211> LENGTH: 5
<212> TYPE: PRT
<213> ORGANISM: L. lactis NRRL B-50571

<400> SEQUENCE: 8

Ala Glu Ser Ile Ser
1               5

<210> SEQ ID NO 9
<211> LENGTH: 7
<212> TYPE: PRT
<213> ORGANISM: L. lactis NRRL B-50571

<400> SEQUENCE: 9

Ser Ile Thr Arg Ile Asn Lys
1               5

<210> SEQ ID NO 10
<211> LENGTH: 9
<212> TYPE: PRT
<213> ORGANISM: L. lactis NRRL B-50571

<400> SEQUENCE: 10

His Ile Gln Lys Glu Asp Val Pro Ser
1               5

<210> SEQ ID NO 11
<211> LENGTH: 9
<212> TYPE: PRT
<213> ORGANISM: L. lactis NRRL B-50571
```

```
<400> SEQUENCE: 11

Thr Val Gln Val Thr Ser Thr Ala Val
1               5

<210> SEQ ID NO 12
<211> LENGTH: 9
<212> TYPE: PRT
<213> ORGANISM: L. lactis NRRL B-50571

<400> SEQUENCE: 12

Asn Ala Val Pro Ile Thr Pro Leu Asn
1               5

<210> SEQ ID NO 13
<211> LENGTH: 8
<212> TYPE: PRT
<213> ORGANISM: L. lactis NRRL B-50571

<400> SEQUENCE: 13

Ser Leu Pro Gln Asn Ile Pro Leu
1               5

<210> SEQ ID NO 14
<211> LENGTH: 16
<212> TYPE: PRT
<213> ORGANISM: L. lactis NRRL B-50571

<400> SEQUENCE: 14

Gln Glu Pro Val Leu Gly Pro Val Arg Gly Pro Phe Pro Ile Ile Val
1               5                   10                  15

<210> SEQ ID NO 15
<211> LENGTH: 11
<212> TYPE: PRT
<213> ORGANISM: L. lactis NRRL B-50571

<400> SEQUENCE: 15

Gly Pro Val Arg Gly Pro Phe Pro Ile Ile Val
1               5                   10

<210> SEQ ID NO 16
<211> LENGTH: 8
<212> TYPE: PRT
<213> ORGANISM: L. lactis NRRL B-50571

<400> SEQUENCE: 16

Tyr Ile Pro Ile Tyr Val Leu Ser
1               5

<210> SEQ ID NO 17
<211> LENGTH: 13
<212> TYPE: PRT
<213> ORGANISM: L. lactis NRRL B-50571

<400> SEQUENCE: 17

Pro Glu Ile Asn Thr Val Gln Val Thr Ser Thr Ala Val
1               5                   10

<210> SEQ ID NO 18
<211> LENGTH: 6
<212> TYPE: PRT
<213> ORGANISM: L. lactis NRRL B-50571
```

```
<400> SEQUENCE: 18

Gly Tyr Leu Ala Val Ala
1               5

<210> SEQ ID NO 19
<211> LENGTH: 12
<212> TYPE: PRT
<213> ORGANISM: L. lactis NRRL B-50572

<400> SEQUENCE: 19

Asp Val Glu Asn Leu His Leu Pro Leu Pro Leu Leu
1               5                   10

<210> SEQ ID NO 20
<211> LENGTH: 5
<212> TYPE: PRT
<213> ORGANISM: L. lactis NRRL B-50572

<400> SEQUENCE: 20

Glu Asn Gly Glu Cys
1               5

<210> SEQ ID NO 21
<211> LENGTH: 8
<212> TYPE: PRT
<213> ORGANISM: L. lactis NRRL B-50572

<400> SEQUENCE: 21

Thr Asp Asp Ile Met Cys Val Lys
1               5

<210> SEQ ID NO 22
<211> LENGTH: 17
<212> TYPE: DNA
<213> ORGANISM: artificial sequence
<220> FEATURE:
<223> OTHER INFORMATION: primer

<400> SEQUENCE: 22
cttcaacaga caagtcc                                                  17

<210> SEQ ID NO 23
<211> LENGTH: 17
<212> TYPE: DNA
<213> ORGANISM: artificial sequence
<220> FEATURE:
<223> OTHER INFORMATION: primer

<400> SEQUENCE: 23
gataaatgat tccaagc                                                  17
```